US011254642B2

(12) United States Patent
Yu et al.

(10) Patent No.: US 11,254,642 B2
(45) Date of Patent: Feb. 22, 2022

(54) METHOD FOR PREPARING 2-CHLORO-5-TRIFLUOROMETHYLPYRIDINE

(71) Applicants: ZHEJIANG LANTIAN ENVIRONMENTAL PROTECTION HI-TECH CO., LTD., Hangzhou (CN); ZHEJIANG RESEARCH INSTITUTE OF CHEMICAL INDUSTRY CO., LTD., Zhejiang (CN); SINOCHEM LANTIAN CO., LTD., Hangzhou (CN)

(72) Inventors: Wanjin Yu, Zhejiang (CN); Shengda Lin, Zhejiang (CN); Minyang Liu, Zhejiang (CN); Wucan Liu, Zhejiang (CN); Jianjun Zhang, Zhejiang (CN); Xianjin Chen, Zhejiang (CN)

(73) Assignees: ZHEJIANG LANTIAN ENVIRONMENTAL PROTECTION HI-TECH CO., LTD., Hangzhou (CN); ZHEJIANG RESEARCH INSTITUTE OF CHEMICAL INDUSTRY CO., LTD., Hangzhou (CN); SINOCHEM LANTIAN CO., LTD., Hangzhou (CN)

( * ) Notice: Subject to any disclaimer, the term of this patent is extended or adjusted under 35 U.S.C. 154(b) by 0 days.

(21) Appl. No.: 16/772,916

(22) PCT Filed: Dec. 5, 2018

(86) PCT No.: PCT/CN2018/119320
§ 371 (c)(1),
(2) Date: Jun. 15, 2020

(87) PCT Pub. No.: WO2019/134477
PCT Pub. Date: Jul. 11, 2019

(65) Prior Publication Data
US 2021/0139428 A1    May 13, 2021

(30) Foreign Application Priority Data

Jan. 5, 2018  (CN) .......................... 201810009294.2
Jan. 5, 2018  (CN) .......................... 201810009301.9
Jan. 5, 2018  (CN) .......................... 201810020465.1

(51) Int. Cl.
*C07D 213/61* (2006.01)
*B01J 23/04* (2006.01)
*B01J 23/44* (2006.01)
*B01J 29/40* (2006.01)

(52) U.S. Cl.
CPC ............ *C07D 213/61* (2013.01); *B01J 23/04* (2013.01); *B01J 23/44* (2013.01); *B01J 29/40* (2013.01)

(58) Field of Classification Search
CPC ...... C07D 213/61; C07D 213/60; B01J 23/04; B01J 23/44; B01J 29/40
See application file for complete search history.

(56) References Cited

U.S. PATENT DOCUMENTS

| 4,257,857 A * | 3/1981 | Whittaker ............ C07D 213/61 204/157.71 |
| 4,259,496 A | 3/1981 | Whittaker |
| 4,266,064 A * | 5/1981 | Nishiyama ........... C07D 213/61 546/345 |
| 4,288,599 A * | 9/1981 | Nishiyama ........... C07D 213/61 546/345 |
| 4,288,600 A * | 9/1981 | Roberts ................ C07D 213/61 546/345 |
| 4,404,388 A * | 9/1983 | Fah ...................... C07D 213/61 203/58 |
| 4,417,055 A | 11/1983 | Nishiyama et al. |

(Continued)

FOREIGN PATENT DOCUMENTS

| CN | 1316423 A | 10/2001 |
| CN | 102452976 A * | 5/2012 |

(Continued)

OTHER PUBLICATIONS

R. Taylor et al., e-EROS Encyclopedia of Reagents for Organic Synthesis (2001) (Year: 2001).*
Jiang, En et al., "Synthesis of 2-Chloro-5-Trifluoromethyl Pyridine (2, 5-CTF)", Organo-Fluorine Industry, Issue No. 1, Mar. 31, 2010, pp. 36-40.
Yu, Wanjin et al., "Synthesis and Market Analysis of 2-Chloro-5-Trifluoromethyl Pyridine", Organo-Fluorine Industry, Issue No. 4, Dec. 31, 2013, pp. 37-41 and 60.

*Primary Examiner* — Alexander R Pagano
(74) *Attorney, Agent, or Firm* — Muncy, Geissler, Olds & Lowe, P.C.

(57) ABSTRACT

The present invention provides a method for the preparing of 2-chloro-5-trifluoromethylpyridine, comprising two steps of chlorofluorination reaction and chlorination reaction, the chlorination catalyst used in the chlorination reaction was chosen from a fluoride, an oxide, a hydroxide, a carbonate, or a chloride of magnesium, calcium and barium and a supported palladium catalyst; or under the action of at least one catalyst chosen from ZSM-5, 5A, β and 13× molecular sieves, 3-trifluoromethylpyridine and chlorine gas phase have reaction to obtain 2-chloro-5-trifluoromethylpyridine. Or, under the action of a catalyst chosen from a fluoride, an oxide, a hydroxide, a carbonate, or a chloride of magnesium, calcium, and barium and a supported palladium catalyst, 3-trifluoromethylpyridine and chlorine gas phase have reaction to obtain 2-chloro-5-trifluoromethylpyridine. The present invention has the advantages of easily availability and low-cost of raw materials, safe operation, high yield, easy isolation and recovery of catalyst, environmental protection, fast reaction speed and continuous production on a large-scale, etc.

15 Claims, No Drawings

(56) References Cited

U.S. PATENT DOCUMENTS

| | | | | |
|---|---|---|---|---|
| 4,429,132 A * | 1/1984 | Whittaker | ............ | C07D 213/61 |
| | | | | 546/345 |
| 4,448,967 A | 5/1984 | Whittaker | | |
| 4,479,001 A * | 10/1984 | Johnston | ................ | A01N 43/40 |
| | | | | 504/256 |
| 4,490,534 A * | 12/1984 | Fujikawa | ............ | C07D 213/61 |
| | | | | 546/345 |
| 4,563,529 A * | 1/1986 | Nishiyama | ........... | C07D 213/61 |
| | | | | 546/345 |
| 4,567,273 A | 1/1986 | Fung | | |
| 4,745,193 A | 5/1988 | Howarth et al. | | |
| 4,752,644 A * | 6/1988 | Sharvit | ................ | C07D 213/61 |
| | | | | 546/345 |
| 6,150,528 A * | 11/2000 | Lantzsch | ............. | C07D 213/61 |
| | | | | 546/329 |
| 7,345,177 B2 * | 3/2008 | Campbell | ............ | C07D 213/16 |
| | | | | 546/345 |
| 8,691,997 B2 * | 4/2014 | Fukui | ................... | C07D 213/61 |
| | | | | 546/345 |
| 2020/0048203 A1 * | 2/2020 | Yoshizawa | ............. | B01J 27/128 |
| 2020/0102273 A1 * | 4/2020 | Yu | ........................ | C07D 213/61 |

FOREIGN PATENT DOCUMENTS

| | | | | |
|---|---|---|---|---|
| CN | 102875454 A * | 1/2013 | | |
| CN | 104610137 A * | 5/2015 | | |
| CN | 105013517 A | 11/2015 | | |
| EP | 0013474 A2 * | 7/1980 | ........... | C07D 213/61 |
| GB | 2045761 A | 11/1980 | | |
| WO | WO-8404904 A1 * | 12/1984 | ............. | B63B 43/04 |
| WO | WO-2005105747 A1 * | 11/2005 | ........... | C07D 213/16 |

* cited by examiner

METHOD FOR PREPARING 2-CHLORO-5-TRIFLUOROMETHYLPYRIDINE

FIELD OF THE INVENTION

The present invention relates to a method for preparing 2-chloro-5-trifluoromethylpyridine.

BACKGROUND

As a very important fluorine-containing pyridine-based chemical raw material, 2-chloro-5-trifluoromethylpyridine can be used in the preparation of trifluoromethylpyridine intermediates for pharmaceuticals, agricultural chemicals and biological agents, for example, synthesis of key intermediates of 2-amino-5-trifluoromethylpyridine, 2-hydroxy-5-trifluoromethylpyridine, 2-mercapto-5-trifluoromethylpyridine and 2,3-dichloro-5-trifluoromethylpyridine, insecticide pyridalyl, high-efficiency herbicide fluazifop-butyl (trade name onecide-p), poppenate-methyl and high-efficiency fungicide fluazinam, etc. These fluorine-containing pesticides have the advantages of broad-spectrum systemic absorption, high efficiency and low toxicity, good safety, and long-lasting effect. They are widely used worldwide and have broad market prospects.

The prior art has the following disclosures for the preparation of 2-chloro-5-trifluoromethylpyridine.

(1) The patents U.S. Pat. No. 4,567,273, CN1316423, U.S. Pat. No. 4,745,193 and GB2045761 reported methods for preparing 2-chloro-5-trifluoromethylpyridine by using 2-chloro-5-trichloromethylpyridine as a starting material in liquid phase. The methods adopt the liquid phase fluorination technology, which have the drawbacks of serious equipment corrosion, high safety hazards, short catalyst life, difficult handling, and large amount of chemical wastes, etc.;

(2) The patents EP0013474, U.S. Pat. No. 4,448,967 and CN201510047137 reported a method for preparing 2-chloro-5-trifluoromethylpyridine using 3-trifluoromethylpyridine as a starting material in the gas phase. Of which, the patent EP0013474 reported that 3-trifluoromethyl was subjected to gas-phase thermal chlorination reaction at a temperature above 380° C. to prepare 2-chloro-5-trifluoromethylpyridine, with a yield of 67%; the patent CN201510047137 reported that ferric chloride supported on activated carbon was used a catalyst and 3-trifluoromethylpyridine was subjected to catalytic chlorination reaction at a temperature of 420° C. to prepare 2-chloro-5-trifluoromethylpyridine, while the yield of 2-chloro-5-trifluoromethylpyridine was not disclosed;

(3) The patents U.S. Pat. Nos. 4,288,599 and 4,417,055 disclosed a method for preparing 2-chloro-5-trifluoromethylpyridine using 3-methylpyridine as a starting material. Of which, the patent U.S. Pat. No. 4,288,599 adopted a fixed bed one-step method, with the highest yield of 42%; the patent U.S. Pat. No. 4,417,055 disclosed a reaction temperature of 400° C., with the highest yield of 53.2%. The method has the drawbacks of low utilization rate of raw materials, large amount of chemical wastes and high energy consumption, etc.

The above preparation methods have the problems of low catalyst selectivity and low activity, resulting in high reaction temperature, low utilization rate of raw materials, large amount of chemical wastes and high energy consumption, etc. Therefore, it is necessary to develop a method for preparing 2-chloro-5-trifluoromethylpyridine with high selectivity and yield and low energy consumption.

SUMMARY

The object of the present invention is to provide a method for preparing 2-chloro-5-trifluoromethylpyridine, with the advantages of easily availability and low-cost of raw materials, safe operation, high yield, easily isolation and recovery of catalyst, environmental protection, fast reaction speed and continuous production on a large-scale, etc.

The abbreviations of the products and reactants in the present invention are as follows:
 3-TF: 3-trifluoromethylpyridine;
 3-MP: 3-methylpyridine;
 2,5-CTF: 2-chloro-5-trifluoromethylpyridine;
 2,3-CTF: 2-chloro-3-trifluoromethylpyridine;
 2,6,3-DCTF: 2,6-dichloro-3-trifluoromethylpyridine.

The present invention provides the following technical solutions.

A method for preparing 2-chloro-5-trifluoromethylpyridine, wherein the method is a two-stage process, comprising:

(1) Chlorofluorination reaction: the temperature of chlorofluorination is maintained at 150-320° C. in the presence of a chlorofluorination catalyst, and 3-methylpyridine, chlorine gas and hydrogen fluoride are introduced to a chlorofluorination reaction zone to obtain a gas mixture containing 3-trifluoromethylpyridine;

(2) Chlorination reaction: the temperature of chlorination is maintained at 220-380° C. in the presence of a chlorination catalyst, and the gas mixture containing 3-trifluoromethylpyridine obtained in the step (1) is introduced into a chlorination reaction zone to obtain 2-chloro-5-trifluoromethylpyridine, the chlorination catalyst is chosen from a fluoride, an oxide, a hydroxide, a carbonate, or a chloride of magnesium, calcium, and barium, and a supported palladium catalyst supported on activated carbon, alumina, or aluminum fluoride.

The above preparation method provided herein is a two-stage process reaction and includes a chlorofluorination reaction step and a chlorination reaction step. In the chlorofluorination reaction step, a chlorofluorination catalyst is used.

The chlorofluorination catalyst may be a chlorofluorination catalyst commonly used in the art.

As a preferred embodiment, the chlorofluorination catalyst comprises a primary catalyst, a first co-catalyst and a second co-catalyst, the primary catalyst is chosen from at least one of aluminum, magnesium and chromium, and the first co-catalyst is chosen from at least one of iron, cobalt, manganese, nickel, copper, bismuth and zinc, the second co-catalyst is chosen from at least one of lanthanum, cerium, barium, calcium, sodium and potassium.

As a further preferred embodiment, for the chlorofluorination catalyst, the primary catalyst is chosen from aluminum and/or chromium, the first co-catalyst is chosen from at least one of iron, nickel and copper, the second co-catalyst is chosen from at least one of lanthanum, barium and calcium.

For the chlorofluorination catalyst, the ratio of the primary catalyst to the first co-catalyst and to the second co-catalyst is sufficient to make the reaction to proceed smoothly.

Preferably, the molar ratio of the primary catalyst to the first co-catalyst and to the second co-catalyst is 50-95:5-42:0.3-8.

More preferably, the molar ratio of the primary catalyst to the first co-catalyst and to the second co-catalyst is 75-90:10-20:1-5.

In the step (1) chlorofluorination reaction of the preparation method provided herein, the ratio of 3-methylpyridine to chloride gas and to hydrogen fluoride is sufficient to make the reaction to proceed smoothly.

Preferably, the molar ratio of 3-methylpyridine to chloride gas and to hydrogen fluoride is 1:0.1-50:1-30.

More preferably, the molar ratio of 3-methylpyridine to chloride gas and to hydrogen fluoride is 1:4-10:3-12.

Wherein, the raw material 3-methylpyridine can be directly added to the reaction in the form of gas, or can be added to the reaction in the form of a gas mixture after being diluted with inert gas.

Preferably, 3-methylpyridine is a gas mixture diluted with inert gas.

Wherein, the ratio of 3-methylpyridine in the gas mixture diluted with inert gas is sufficient to make the reaction to proceed smoothly.

Preferably, the molar ratio of 3-methylpyridine to gas mixture is 1:0.5-50.

More preferably, the molar ratio of 3-methylpyridine to gas mixture is 1:5-20.

In the step (1) chlorofluorination reaction of the preparation method provided herein, the contact time of 3-methylpyridine, chloride gas and hydrogen fluoride with the chlorofluorination catalyst is sufficient to make the reaction to proceed smoothly.

Preferably, the contact time of 3-methylpyridine, chloride gas and hydrogen fluoride with the chlorofluorination catalyst is 0.5-40 s.

More preferably, the contact time of 3-methylpyridine, chloride gas and hydrogen fluoride with the chlorofluorination catalyst is 1.5-20 s.

In the step (2) chlorination reaction of the preparation method provided herein, the chlorination catalyst is chosen from a fluoride, an oxide, a hydroxide, a carbonate, or a chloride of magnesium, calcium, and barium, and a supported palladium catalyst supported on activated carbon, alumina, or aluminum fluoride.

The magnesium, calcium, and barium fluorides, oxides, hydroxides, carbonates and chlorides may be magnesium fluoride, calcium fluoride, barium fluoride, magnesium oxide, calcium oxide, barium oxide, magnesium hydroxide, calcium hydroxide, barium hydroxide, magnesium carbonate, calcium carbonate, barium carbonate, magnesium chloride, calcium chloride, barium chloride.

The supported palladium catalyst supported on activated carbon, alumina, or aluminum fluoride may be a supported palladium catalyst supported on activated carbon, a supported palladium catalyst supported on alumina, or a supported palladium catalyst supported on aluminum fluoride.

Preferably, the chlorination catalyst is chosen from a fluoride, an oxide or a chloride of magnesium, calcium, and a supported palladium catalyst supported on activated carbon or aluminum fluoride.

In the step (2) chlorination reaction of the preparation method provided herein, the contact time of the gas mixture containing 3-trifluoromethylpyridine with the chlorination catalyst is sufficient to make the reaction to proceed smoothly.

Preferably, the contact time of the gas mixture containing 3-trifluoromethylpyridine with the chlorination catalyst is 0.5-40 s.

More preferably, the contact time of the gas mixture containing 3-trifluoromethylpyridine with the chlorination catalyst is 1.5-20 s.

The preparation method provided herein is a two-stage process, comprising a chlorofluorination reaction step and a chlorination reaction step, and the temperature control of the two steps has an effect on the reaction result.

Preferably, the temperature of chlorofluorination is 150-320° C. and the temperature of chlorination 220-380° C.

More preferably, the temperature of chlorofluorination is 220-260° C. and the temperature of chlorination is 270-320° C.

In the preparation method provided herein, preferably, the reaction is carried out in a fixed bed or fluidized bed reactor.

In the preparation method provided herein, the yields of products are calculated according to the following formula.

The yield of the product i:

$$Y_i=(m_i/M_i)/(m_{3\text{-}MP}/M_{3\text{-}MP})*100\%.$$

The yield of other products:

$$Y_{other}=(1-\Sigma Y_i)*100\%$$

Where, i represents four substances, namely: 3-TF, 2,5-CTF, 2,3-CTF, and 2,6,3-DCTF. Other products include by-products of insufficient chlorofluorination of the side chain methyl chloride and excessive chlorination on the ring, etc. as well as substances lost during the experiments. Since the conversion rate of 3-methylpyridine is 100% under the given reaction conditions in the following examples, the yield of the product i is the selectivity of the product I in the present invention.

The above method has the following advantages over the prior art. By designing and using chlorofluorination catalyst and chlorination catalyst, the selectivity and yield of the target product 2-chloro-5-trifluoromethylpyridine are increased up to 76.7%; the gas from the first-stage reaction zone directly enters the second-stage reaction zone for reaction without requiring cooling, separation, and re-vaporization, with simple operation and low energy consumption. Through the two-stage reactions, each stage has a low reaction temperature and low content of by-products.

In order to achieve the above object, the present invention further provides the following method for preparing 2-chloro-5-trifluoromethylpyridine, which has the characteristics of high conversion of raw materials, high selectivity of target products, low reaction temperature, low energy consumption, simple separation, and no need to use organic solvents, initiators and photochlorination reactor equipment, etc.

The present invention provides a method for preparing 2-chloro-5-trifluoromethylpyridine, and the chemical reaction formula is as follows:

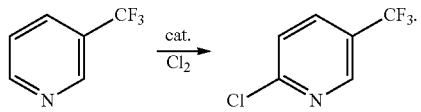

The present invention provides the following technical solutions:

A method for preparing 2-chloro-5-trifluoromethylpyridine, wherein the method comprising:

the reaction temperature is maintained at 150-350° C. in the presence of a first catalyst, such that 3-trifluoromethylpyridine reacts with chlorine gas in gas phase to obtain 2-chloro-5-trifluoromethylpyridine;

the first catalyst is chosen from at least one of ZSM-5, 5A, β and 13× molecular sieves, the Si/Al of the ZSM-5 molecular sieve is 50-300, and the balance cation is chosen from at least one of H$^+$, Na$^+$, K$^+$, Ca$^{2+}$.

In the preparation method provided herein, the first catalyst used is chosen from at least one of ZSM-5, 5A, β and 13× molecular sieves.

When the first catalyst is a ZSM-5 molecular sieve, as a preferred embodiment, the Si/Al is 50-300, and the balance cation is chosen from at least one of H$^+$, Na$^+$, K$^+$ and Ca$^{2+}$.

As a further preferred embodiment, the Si/Al of the ZSM-5 molecular sieve is 80-200, and the balance cation is chosen from at least one of H$^+$, Na$^+$ and K$^+$.

In the preparation method provided herein, the reaction temperature is sufficient to make the reaction to proceed smoothly.

Preferably, the reaction temperature is 150-350° C.

More preferably, the reaction temperature is 200-300° C.

In the preparation method provided herein, the molar ratio of 3-trifluoromethylpyridine to chlorine gas is sufficient to make the reaction to proceed smoothly.

Preferably, the molar ratio of 3-trifluoromethylpyridine to chlorine gas is 1:0.1-20.

More preferably, the molar ratio of 3-trifluoromethylpyridine to chlorine gas is 1:0.5-5.

In the preparation method provided herein, the contact time of 3-trifluoromethylpyridine and chlorine gas with the catalyst bed is sufficient to make the reaction to proceed smoothly.

Preferably, the contact time of 3-trifluoromethylpyridine and chlorine gas with the catalyst bed is 0.5-100 s.

More preferably, the contact time of 3-trifluoromethylpyridine and chlorine gas with the catalyst bed is 15-70 s.

In the preparation method provided herein, the reaction can be carried out in a fixed bed or fluidized bed reactor.

Preferably, the reaction is carried out in a fluidized bed reactor.

The material of the reactor can be quartz tube and Inconel alloy, etc.

The above method has the following advantages over the prior art. The selectivity to the target product 2-chloro-5-trifluoromethylpyridine and the atom economy is high; the raw material 3-trifluoromethylpyridine is fed directly, and there is no need to use organic diluent or carry out additional vaporization and separation of the diluent; the reaction temperature is low and the energy consumption is low.

In order to achieve the above object, the present invention further provides a method for preparing 2-chloro-5-trifluoromethylpyridine, which has the characteristics of high conversion of raw materials, high selectivity to target products, low reaction temperature, low energy consumption, simple separation, and no need to use organic solvents, initiators and photochlorination reactor equipment, etc.

The present invention provides a method for preparing 2-chloro-5-trifluoromethylpyridine, and the chemical reaction formula is as follows:

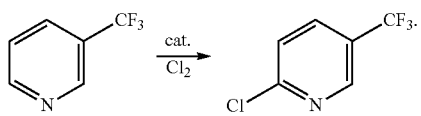

The present invention provides the following technical solutions:

A method for preparing 2-chloro-5-trifluoromethylpyridine, wherein the method comprising:

the reaction temperature is maintained at 220-360° C. in the presence of a second catalyst, such that 3-trifluoromethylpyridine and chlorine pass through a catalyst bed to obtain 2-chloro-5-trifluoromethylpyridine;

The second catalyst is chosen from a fluoride, an oxide, a hydroxide, a carbonate, or a chloride of magnesium, calcium, and barium, and a supported palladium catalyst supported on activated carbon, alumina, or aluminum fluoride.

In the preparation method provided herein, the second catalyst used is chosen from a fluoride, an oxide, a hydroxide, a carbonate, or a chloride of magnesium, calcium, and barium, and a supported palladium catalyst supported on activated carbon, alumina, or aluminum fluoride.

The magnesium, calcium, and barium fluorides, oxides, hydroxides, carbonates and chlorides may be magnesium fluoride, calcium fluoride, barium fluoride, magnesium oxide, calcium oxide, barium oxide, magnesium hydroxide, calcium hydroxide, barium hydroxide, magnesium carbonate, calcium carbonate, barium carbonate, magnesium chloride, calcium chloride, barium chloride.

The supported palladium catalyst supported on activated carbon, alumina, or aluminum fluoride may be a supported palladium catalyst supported on activated carbon, a supported palladium catalyst supported on alumina, or a supported palladium catalyst supported on aluminum fluoride.

As a preferred embodiment, the second catalyst is chosen from a fluoride, an oxide or a chloride of magnesium, calcium, and a palladium catalyst supported on activated carbon or aluminum fluoride.

When the second catalyst used is a supported palladium catalyst supported on activated carbon, alumina, or aluminum fluoride, the mass percentage of palladium in the catalyst is sufficient to make the reaction to proceed smoothly.

Preferably, the mass percentage of palladium in the catalyst is 0.1-10 wt %.

More preferably, the mass percentage of palladium in the catalyst is 0.5-3 wt %.

When the second catalyst used is a supported palladium catalyst supported on activated carbon, alumina, or aluminum fluoride, as a preferred embodiment, activation pretreatment is performed before use.

The activation pretreatment may be activation pretreatment of the supported palladium catalyst using nitrogen and/or chlorine gas at a temperature of 120-350° C.

In the preparation method provided herein, the reaction temperature is sufficient to make the reaction to proceed smoothly.

Preferably, the reaction temperature is 220-360° C.

More preferably, the reaction temperature is 270-320° C.

In the preparation method provided herein, the molar ratio of 3-trifluoromethylpyridine to chlorine gas is sufficient to make the reaction to proceed smoothly.

Preferably, the molar ratio of 3-trifluoromethylpyridine to chlorine gas is 1:0.1-50.

More preferably, the molar ratio of 3-trifluoromethylpyridine to chlorine gas is 1:4-10.

In the preparation method provided herein, the contact time of 3-trifluoromethylpyridine and chlorine gas with the catalyst bed is sufficient to make the reaction to proceed smoothly.

Preferably, the contact time of 3-trifluoromethylpyridine and chlorine gas with the catalyst bed is 1-60 s.

More preferably, the contact time of 3-trifluoromethylpyridine and chlorine gas with the catalyst bed is 5-30 s.

In the preparation method provided herein, the reaction can be carried out in a fixed bed or fluidized bed reactor.

Preferably, the reaction is carried out in a fluidized bed reactor.

In the preparation method provided herein, the prepared product is subjected to water scrubbing, alkaline cleaning and distillation, to obtain an oily product, namely, 2-chloro-5-trifluoromethylpyridine.

The above method has the following advantages over the prior art. The selectivity to the target product 2-chloro-5-trifluoromethylpyridine and the atom economy is high; the raw material 3-trifluoromethylpyridine is fed directly, and there is no need to use organic diluent or carry out additional vaporization and separation of the diluent; the reaction temperature is low and the energy consumption is low.

DETAILED DESCRIPTION

The present invention will be further described below in conjunction with specific embodiments, but the present invention is not limited to these specific embodiments. Those skilled technicians should be aware that the present invention covers all alternatives, improvements and equivalents that may be included within the scope of the appended claims.

Example 1

The oven of the heating furnace having an inner diameter of 30 mm and a height of 600 mm was used, and the upper and lower sections were temperature-controlled separately. The upper section was a chlorofluorination reaction zone, and the lower section was a chlorination reaction zone. A stainless steel reaction tube having an inner diameter of 19 mm and a length of 700 mm was used. The packing height of the upper and lower catalysts was both 140 mm, and the upper and lower catalyst beds were in the constant temperature zone of the upper and lower heating furnaces. The chlorofluorination catalyst bed was composed of catalyst of 55.5% $MgF_2$-40.0% $Co_2O_3$-0.55% $CeO_2$ (55.5%, 40%, 0.5% was the molar percentage of metal atoms, which was the ratio of moles of metal atoms of each component to the sum of the moles of metal atoms, the composition of chlorofluorination catalyst was represented by the molar ratio of metal atoms, the same below). The catalyst was formed into a cylinder with a diameter of 3 mm and a height of 4 mm. The chlorination catalyst bed was composed of 1% Pd/activated carbon catalyst (1% was the mass proportion of metal palladium in the calcined catalyst. The composition of the supported chlorination catalyst was represented by the ratio of the mass of metal atoms to the total mass of the catalyst, the same below), and the catalyst was formed into a cylinder with a diameter of 3 mm and a height of 4 mm.

The chlorofluorination reaction zone was heated to 235° C. and the chlorination reaction zone was heated to 290° C. A stream of anhydrous hydrogen fluoride (10.00 g/h, 0.500 mol/h), was introduced to activate the catalyst for 3 hours, and then a stream of 3-methylpyridine (4.00 g/h, 0.043 mol/h, vaporized with nitrogen) and chlorine (7.7 L/h, 0.344 mol/h) were introduced into the reaction tube. The feeding molar ratio of the reactants was: 3-methylpyridine:chlorine gas:hydrogen fluoride:nitrogen gas=1:8:11.6:12.5. The contact time of all starting reaction materials with the chlorofluorination catalyst bed and the chlorination catalyst bed catalyst was 4.5 s, and the reaction was carried out for 8 hours.

The gaseous reactor effluent was introduced into a water scrubber and an alkaline tower for condensation. The resulting oil layer was separated and neutralized with ammonia water, and subjected to steam distillation to obtain an oily product. The obtained oily product was dried over anhydrous sodium sulfate and weighed 63.04 g, and then was quantitatively analyzed by gas chromatography (internal standard method). The mass content of 2,5-CTF was 70.8% and the reaction yield was 71.5% (calculated based on 3-MP, same below).

Example 2

In the reaction tube described in Example 1, the upper section was packed with 55.5% $MgF_2$-40% ZnO-0.5% $K_2O$ catalyst, and the catalyst was formed into a cylinder with a diameter of 3 mm and a height of 4 mm. The lower section was packed with 2% Pd/activated carbon catalyst, and the catalyst was formed into a cylinder with a diameter of 3 mm and a height of 4 mm.

The chlorofluorination reaction zone was heated to 265° C. and the chlorination reaction zone was heated to 320° C. The anhydrous hydrogen fluoride was fed at a controlled rate of 10.00 g/h (0.500 mol/h), and HF was introduced to activate the catalyst for 3 hours, and then 3-methylpyridine (vaporized with nitrogen as the carrier gas) and chlorine were introduced into the reaction tube. Of which, the flow rate of 3-methylpyridine was controlled at 4.00 g/h (0.043 mol/h), the flow rate of chlorine was controlled at 7.7 L/h (0.344 mol/h) and the flow rate of nitrogen was maintained at 12.0 L/h (0.536 mol/h). The feeding molar ratio of the reactants was: 3-methylpyridine:chlorine gas:hydrogen fluoride:nitrogen gas=1:8:11.6:12.5. The contact time of all starting reaction materials with the chlorofluorination catalyst bed and the chlorination catalyst bed catalyst was 4.5 s, and the reaction was carried out for 8 hours.

The gaseous reactor effluent was treated according to the way as Example 1, and 64.35 g of oily product was obtained, and then quantitatively analyzed by gas chromatography. The mass content of 2,5-CTF was 65.7% and the reaction yield was 67.8%.

Example 3

In the reaction tube described in Example 1, the upper section was packed with 77.0% $MgF_2$-20.0% $Bi_2O_3$-2.0% $Na_2O$ catalyst, and the catalyst was formed into a cylinder with a diameter of 3 mm and a height of 4 mm. The lower section was packed with $MgF_2$ catalyst, and the catalyst was formed into a cylinder with a diameter of 3 mm and a height of 4 mm.

The chlorofluorination reaction zone was heated to 220° C. and the chlorination reaction zone was heated to 280° C. The anhydrous hydrogen fluoride was fed at a controlled rate of 10.00 g/h (0.500 mol/h), and HF was introduced to activate the catalyst for 3 hours, and then 3-methylpyridine (vaporized with nitrogen as the carrier gas) and chlorine were introduced into the reaction tube. Of which, the flow rate of 3-methylpyridine was controlled at 4.00 g/h (0.043 mol/h), the flow rate of chlorine was controlled at 7.7 L/h (0.344 mol/h) and the flow rate of nitrogen was maintained at 12.0 L/h (0.536 mol/h). The feeding molar ratio of the reactants was: 3-methylpyridine:chlorine gas:hydrogen fluoride:nitrogen gas=1:8:11.6:12.5. The contact time of all starting reaction materials with the chlorofluorination catalyst bed and the chlorination catalyst bed catalyst was 4.5 s, and the reaction was carried out for 8 hours.

The gaseous reactor effluent was treated according to the way as Example 1, and 61.94 g of oily product was obtained, and then quantitatively analyzed by gas chromatography. The mass content of 2,5-CTF was 77.2% and the reaction yield was 76.7%.

Example 4

In the reaction tube described in Example 1, the upper section was packed with 85.0% $CrF_3$-10.0% CuO-5.0% $La_2O_3$ catalyst, and the catalyst was formed into a cylinder with a diameter of 3 mm and a height of 4 mm. The lower section was packed with MgO catalyst, and the catalyst was formed into a cylinder with a diameter of 3 mm and a height of 4 mm.

The chlorofluorination reaction zone was heated to 235° C. and the chlorination reaction zone was heated to 300° C. The anhydrous hydrogen fluoride was fed at a controlled rate of 10.32 g/h (0.516 mol/h), and HF was introduced to activate the catalyst for 3 hours, and then 3-methylpyridine (vaporized with nitrogen) and chlorine were introduced into the reaction tube. Of which, the flow rate of 3-methylpyridine was controlled at 4.00 g/h (0.043 mol/h), the flow rate of chlorine was controlled at 8.7 L/h (0.387 mol/h) and the flow rate of nitrogen was maintained at 12.0 L/h (0.536 mol/h). The feeding molar ratio of the reactants was: 3-methylpyridine:chlorine gas:hydrogen fluoride:nitrogen gas=1:9:12:12.5. The contact time of all starting reaction materials with both the chlorofluorination catalyst bed and the chlorination catalyst bed catalyst was 4.0 s, and the reaction was carried out for 6 hours.

The gaseous reactor effluent was treated according to the way as Example 1, and 40.50 g of oily product was obtained, and then quantitatively analyzed by gas chromatography. The mass content of 2,5-CTF was 69.7% and the reaction yield was 74.5%.

Examples 5-7

Operation conditions were the same as in Example 3 except for the catalyst. In Example 5, the upper section of the reaction tube was packed with 90.0% $CrF_3$-8.0% $Fe_2O_3$-2.0% $La_2O_3$ catalyst, and the lower section was packed with $BaCl_2$ catalyst; in Example 6, the upper section of the reaction tube was packed with 90.0% $AlF_3$-8.0% NiO-2.0% BaO catalyst, and the lower section was packed with $CaCl_2$ catalyst; in Example 7, the upper section of the reaction tube was packed with 90.0% $CrF_3$-8.0% NiO-2.0% $Na_2O$ catalyst, and the lower section was packed with 1.5% Pd/activated carbon catalyst.

In Examples 5 to 7, 64.30 g, 65.34 g, 64.80 g oily products were obtained respectively, and then the products were quantitatively analyzed by gas chromatography. The mass contents of 2,5-CTF were 73.2%, 69.9% and 73.3% respectively, and the reaction yields were 75.5%, 73.2% and 76.1% respectively.

Example 8

The oven of the heating furnace has an inner diameter of 35 mm and a height of 500 mm, and the upper and lower sections were temperature-controlled separately. The lower section was a chlorofluorination reaction zone, and the upper section was a chlorination reaction zone. The reaction tube was made of Inconel alloy, and it has an inner diameter of 30 mm and a length of 600 mm. The lower section of the reaction tube was packed with 60 mL 85% $AlF_3$-10% $Mn_2O_3$-5% BaO (average particle size of 0.15 mm) chlorofluorination catalyst, the static bed height was 89 mm, and the upper section of the reaction tube was packed with 60 mL 1% Pd/activated carbon (the average particle size of 0.15 mm) chlorination catalyst, the static bed height was 89 mm. A distribution plate was placed at the bottom and the middle of the reactor to distribute the gas flow and isolate and support the catalyst. After fluidizing with nitrogen at 235° C. for 1 h, the catalyst was fluorinated by introducing HF (8.59 g/h, 0.430 mol/h) for 4 h. Afterwards, 3-methylpyridine (vaporized with nitrogen) and chlorine gas were introduced into the reaction tube. Of which, the flow rate of 3-methylpyridine was controlled at 4.00 g/h (0.043 mol/h), the flow rate of chlorine was controlled at 5.77 L/h (0.258 mol/h) and the flow rate of nitrogen was maintained at 9.62 L/h (0.430 mol/h). The feeding molar ratio of the reactants was: 3-methylpyridine:chlorine gas:hydrogen fluoride:nitrogen gas=1:6:10:10. The contact time of all starting reaction materials with the chlorofluorination catalyst bed and the chlorination catalyst bed catalyst was 5.5 s, and the reaction was carried out for 24 hours.

The gaseous reactor effluent was introduced into a water scrubber and an alkaline tower for condensation. The resulting oil layer was separated and neutralized with ammonia water, and subjected to steam distillation to obtain an oily product. The obtained oily product was dried over anhydrous sodium sulfate and weighed 166.49 g, and then quantitatively analyzed by gas chromatography (internal standard method). The mass content of 2,5-CTF was 67.3% and the reaction yield was 73.9%.

Example 9

Operation conditions were the same as in Example 8 except for the catalyst. The lower section of the reaction tube was packed with 60 mL of 90% AlF3-9% ZnCl2-1% CaO (average particle size of 0.15 mm) chlorofluorination catalyst, the upper section was packed with 60 mL of 1% Pd/Al2O3 (average particle size of 0.15 mm) chlorination catalyst. The product treatment and analysis method was the same as those in Example 8, and 158.90 g of oily product was obtained. The mass content of 2,5-CTF was 68.8% and the reaction yield was 72.1%.

Example 10

A stainless steel tube with an inner diameter of 25 mm and a length of 800 mm was used as a fixed-bed reactor. The HZSM-5 ($H^+$ as a balanced cation) molecular sieve with a volume of 40 mL and a particle size of 5-10 meshes and Si/Al of 100 was packed into the middle of the fixed-bed reactor, the reaction line was connected and nitrogen gas was introduced for purging, with a nitrogen flow rate of 100 mL/min. The reaction furnace was heated to 290° C. at a heating rate of 5° C./min. After the catalyst bed reaches the reaction temperature, the nitrogen purging was stopped and switched to chlorine purging, and at the same time, 3-trifluoromethylpyridine was continuously fed into the fixed-bed reactor to start reaction. The molar ratio of reaction material 3-trifluoromethylpyridine to chlorine gas was 1:2, and the contact time of reaction materials with the catalyst bed was 30.9 s. The reaction product was condensed in an ice water bath and collected in a collection bottle to obtain an oily product. After the reaction, the oily product was subjected to water scrubbing and alkaline cleaning to remove the acid, dried over anhydrous sodium sulfate, and then distilled. GC-MS was used for qualitative analysis of the fraction, and gas chromatography (internal standard method) was used for quantitative analysis of the fractional compositions.

The quantitative analysis results showed that the conversion rate of 3-trifluoromethylpyridine was 98.7% and the selectivity of 2-chloro-5-trifluoromethylpyridine was 93.8%.

Example 11

Operation conditions were the same as in Example 10 except for the catalyst. The catalyst used was 5A molecular sieve.

The quantitative analysis results showed that the conversion rate of 3-trifluoromethylpyridine was 89.2% and the selectivity of 2-chloro-5-trifluoromethylpyridine was 89.0%.

Example 12

Operation conditions were the same as in Example 10 except for the catalyst. The catalyst used was 13× molecular sieve.

The quantitative analysis results showed that the conversion rate of 3-trifluoromethylpyridine was 91.5% and the selectivity of 2-chloro-5-trifluoromethylpyridine was 88.3%.

Example 13

Operation conditions were the same as in Example 10 except for the catalyst. The catalyst used was β molecular sieve.

The quantitative analysis results showed that the conversion rate of 3-trifluoromethylpyridine was 92.3% and the selectivity of 2-chloro-5-trifluoromethylpyridine was 89.2%.

Example 14

Operation conditions were the same as in Example 10 except for the reaction temperature. The reaction temperature was 350° C.

The quantitative analysis results showed that the conversion rate of 3-trifluoromethylpyridine was 99.9% and the selectivity of 2-chloro-5-trifluoromethylpyridine was 87.1%.

Example 15

The reaction tube was made of Inconel alloy and has an inner diameter of 30 mm and a length of 400 mm. The reaction tube was packed with 60 mL of HZSM-5 molecular sieve catalyst with an average particle size of 0.15 mm and Si/Al of 100. After fluidizing with nitrogen at 235° C. for 1 h, the temperature was raised to 290° C. at a heating rate of 5° C./min. After the catalyst bed reaches the reaction temperature, the nitrogen purging was stopped and then switched to chlorine purging, and at the same time, 3-trifluoromethylpyridine was continuously fed into the fixed-bed reactor to start reaction. The molar ratio of reaction material 3-trifluoromethylpyridine to chlorine gas was 1:2, and the contact time of reaction materials with the catalyst bed was 58.5 s. The reaction product was condensed in an ice water bath and collected in a collection bottle to obtain an oily product. After the reaction, the oily product was subjected to water scrubbing and alkaline cleaning to remove the acid, dried over anhydrous sodium sulfate, and then distilled. GC-MS was used for qualitative analysis of the fraction, and gas chromatography (internal standard method) was used for quantitative analysis of the fractional compositions.

The quantitative analysis results showed that the conversion rate of 3-trifluoromethylpyridine was 97.9% and the selectivity of 2-chloro-5-trifluoromethylpyridine was 94.5%.

Example 16

Operation conditions were the same as in Example 15 except for the catalyst. The catalyst used was HZSM-5 molecular sieve with Si/Al=50

The quantitative analysis results showed that the conversion rate of 3-trifluoromethylpyridine was 99.0% and the selectivity of 2-chloro-5-trifluoromethylpyridine was 90.1%.

Example 17

Operation conditions were the same as in Example 15 except for the catalyst. The catalyst used was NaZSM-5 molecular sieve ($Na^+$ as a balance cation) with Si/Al=100.

The quantitative analysis results showed that the conversion rate of 3-trifluoromethylpyridine was 95.7% and the selectivity of 2-chloro-5-trifluoromethylpyridine was 92.5%.

Example 18

Operation conditions were the same as in Example 15 except for the catalyst. The catalyst used was KZSM-5 molecular sieve ($K^+$ as a balance cation) with Si/Al=100.

The quantitative analysis results showed that the conversion rate of 3-trifluoromethylpyridine was 92.3% and the selectivity of 2-chloro-5-trifluoromethylpyridine was 92.0%.

Example 19

Operation conditions were the same as in Example 15 except for the catalyst. The catalyst used was CaZSM-5 molecular sieve ($Ca^{2+}$ as a balance cation) with Si/Al=100.

The quantitative analysis results showed that the conversion rate of 3-trifluoromethylpyridine was 94.4% and the selectivity of 2-chloro-5-trifluoromethylpyridine was 88.1%.

Example 20

Operation conditions were the same as in Example 10 except for the chlorine ratio. The molar ratio of 3-trifluoromethylpyridine to chlorine gas was 1:10.

The quantitative analysis results showed that the conversion rate of 3-trifluoromethylpyridine was 98.5% and the selectivity of 2-chloro-5-trifluoromethylpyridine was 85.2%.

Comparative Example 1

Operation conditions were the same as in Example 10 except for the catalyst. The catalyst was changed to HZSM-5 molecular sieve with Si/Al of 22.

The quantitative analysis results showed that the conversion rate of 3-trifluoromethylpyridine was 99.9% but the selectivity of the target product 2-chloro-5-trifluoromethylpyridine was only 47.3%.

Comparative Example 2

According to the disclosure of Chinese patent CN104610137, $FeCl_3$/activated carbon catalyst was used as a catalyst, and the reaction temperature was controlled at 250° C. The remaining operation conditions were the same as in Example 10.

The quantitative analysis results showed that the conversion rate of 3-trifluoromethylpyridine was 96.2% but the selectivity of the target product 2-chloro-5-trifluoromethylpyridine was only 20.2%.

Example 21

The oven of the heating furnace has an inner diameter of 30 mm and a height of 600 mm. The reaction tube has an inner diameter of 19 mm and a length of 700 mm. It was made of stainless steel, the packing height of the catalyst was 140 mm. The catalyst bed was composed of 1% Pd/activated carbon catalyst (1% was the mass proportion of metal palladium in the calcined catalyst, the composition of the supported chlorination catalyst was expressed by the ratio of the mass of metal atoms to the total mass of the catalyst, same below), the catalyst was formed into a cylinder with a diameter of 3 mm and a height of 4 mm. The reaction zone was heated to 290° C., and the vaporized 3-trifluoromethylpyridine and chlorine gas were introduced into the reaction tube. Of which, the flow rate of 3-trifluoromethylpyridine was controlled to 6.33 g/h (0.043 mol/h), and the flow rate of chlorine gas was controlled to 7.7 L/h (0.344 mol/h). The feeding molar ratio of the reactants was: 3-trifluoromethylpyridine:chlorine gas=1:8. The contact time of all starting reaction materials with the catalyst bed was 16.5 s, and the reaction was carried out for 8 hours.

The gaseous reactor effluent was introduced into a water scrubber and an alkaline tower for condensation. The resulting oil layer was separated and neutralized with ammonia water, and subjected to steam distillation to obtain an oily product. The obtained oily product was dried over anhydrous sodium sulfate and weighed 66.28 g, and then quantitatively analyzed by gas chromatography (internal standard method). The mass content of 2-chloro-5-trifluoromethylpyridine was 88.7% and the yield was 94.1% (calculated based on 3-trifluoromethylpyridine, same below).

Example 22

The reaction tube described in Example 21 was packed with a 2% Pd/activated carbon catalyst, and the catalyst was formed into a cylinder with a diameter of 3 mm and a height of 4 mm. The reaction zone was heated to 320° C., and the vaporized 3-trifluoromethylpyridine and chlorine gas were introduced into the reaction tube. Of which, the flow rate of 3-trifluoromethylpyridine was controlled to 6.33 g/h (0.043 mol/h), and the flow rate of chlorine gas was controlled to 7.7 L/h (0.344 mol/h). The feeding molar ratio of the reactants was: 3-trifluoromethylpyridine:chlorine gas=1:8. The contact time of all starting reaction materials with the catalyst bed was 16.5 s, and the reaction was carried out for 8 hours.

The gaseous reactor effluent was treated according to the way as Example 21, and 67.59 g of oily product was obtained, and then quantitatively analyzed by gas chromatography. The mass content of 2-chloro-5-trifluoromethylpyridine was 84.8% and the yield was 91.7%.

Example 23

The reaction tube described in Example 21 was packed with $MgF_2$ catalyst, and the catalyst was formed into a cylinder with a diameter of 3 mm and a height of 4 mm. The reaction zone was heated to 280° C., and the vaporized 3-trifluoromethylpyridine and chlorine gas were introduced into the reaction tube. Of which, the flow rate of 3-trifluoromethylpyridine was controlled to 6.33 g/h (0.043 mol/h), and the flow rate of chlorine gas was controlled to 7.7 L/h (0.344 mol/h). The feeding molar ratio of the reactants was: 3-trifluoromethylpyridine:chlorine gas=1:8. The contact time of all starting reaction materials with the catalyst bed was 16.5 s, and the reaction was carried out for 8 hours.

The gaseous reactor effluent was treated according to the way as Example 21, and 65.86 g of oily product was obtained, and then quantitatively analyzed by gas chromatography. The mass content of 2-chloro-5-trifluoromethylpyridine was 87.8% and the yield was 92.5%.

Example 24

The reaction tube described in Example 21 was packed with MgO catalyst, and the catalyst was formed into a cylinder with a diameter of 3 mm and a height of 4 mm. The reaction zone was heated to 300° C., and the vaporized 3-trifluoromethylpyridine and chlorine gas were introduced into the reaction tube. Of which, the flow rate of 3-trifluoromethylpyridine was controlled to 6.33 g/h (0.043 mol/h), and the flow rate of chlorine gas was controlled to 8.7 L/h (0.387 mol/h). The feeding molar ratio of the reactants was: 3-trifluoromethylpyridine:chlorine gas=1:9. The contact time of all starting reaction materials with the catalyst bed was 14.8 s, and the reaction was carried out for 6 hours.

The gaseous reactor effluent was treated according to the way as Example 21, and 48.49 g of oily product was obtained, and then quantitatively analyzed by gas chromatography. The mass content of 2-chloro-5-trifluoromethylpyridine was 86.7% and the yield was 89.6%.

Examples 25-27

Operation conditions were the same as in Example 23 except for the catalyst. In Example 25, the reaction tube was packed with $BaCl_2$ catalyst; in Example 26, the reaction tube was packed with $CaCl_2$ catalyst; in Example 27, the reaction tube was packed with 1.5% Pd/activated carbon catalyst. In examples 25 to 27, 66.25 g, 61.49 g and 64.57 g oily products were obtained respectively, and the products were quantitatively analyzed by gas chromatography. The mass contents of 2-chloro-5-trifluoromethylpyridine were 85.0%, 89.5% and 89.8%, respectively, and the yields were 90.1%, 88.0% and 92.8%, respectively.

Example 28

The oven of the heating furnace has an inner diameter of 35 mm and a height of 500 mm. The reaction tube was made of Inconel alloy, and it has an inner diameter of 30 mm and a length of 600 mm. The reaction tube was packed with 60 mL 1% Pd/activated carbon (average particle size of 0.15 mm) chlorination catalyst, and the static bed height was 89 mm. After fluidizing with nitrogen at 235° C. for 1 hour, the vaporized 3-trifluoromethylpyridine and chlorine gas were introduced into the reaction tube. Of which, the flow rate of 3-trifluoromethylpyridine was controlled to 6.33 g/h (0.043 mol/h), the flow rate of chlorine gas was controlled to 5.77 L/h (0.258 mol/h), and the flow rate of nitrogen gas was maintained at 9.62 L/h (0.430 mol/h). The feeding molar ratio of the reactants was: 3-trifluoromethylpyridine:chlorine gas=1:6. The contact time of all starting reaction materials with the catalyst bed was 13.5 s, and the reaction was carried out for 24 hours.

The gaseous reactor effluent was introduced into a water scrubber and an alkaline tower for condensation. The resulting oil layer was separated and neutralized with ammonia water, and subjected to steam distillation to obtain an oily product. The obtained oily product was dried over anhydrous sodium sulfate and weighed 185.88 g, and then quantitatively analyzed by gas chromatography (internal standard method). The mass content of 2-chloro-5-trifluoromethylpyridine was 95.8% and the yield was 94.9%.

Example 29

Operation conditions were the same as in Example 28 except for the catalyst. The reaction tube was packed with 60 mL of 1% Pd/$Al_2O_3$ chlorination catalyst (average particle size of 0.15 mm). The product processing and analysis method were the same as those in Example 28, and 179.69 g oily product was obtained. The mass content of 2-chloro-5-trifluoromethylpyridine by chromatographic analysis was 94.6% and the yield was 90.7%.

According to the above comparative examples and the prior art, for example, in Example 4 of the patent U.S. Pat. No. 4,417,055, the highest content of 2-chloro-5-trifluoromethylpyridine was only 58.1%, the corresponding highest yield was 53.2%, and the required reaction temperature was 400° C. The preparation method provided by the present invention significantly improves the yield and selectivity of the target product 2-chloro-5-trifluoromethylpyridine, and the yield of target product can be up to more than 70%. The method provided by the present invention can reduce the unit consumption of the product and the separation cost; moreover, the reaction temperature is far less than 400° C., which can significantly reduce energy consumption and improve safety.

The invention claimed is:

1. A method for preparing 2-chloro-5-trifluoromethylpyridine, wherein the method is a two-stage process, comprising:
   (1) Chlorofluorination reaction: a temperature of chlorofluorination is maintained at 150-320° C. in the presence of a chlorofluorination catalyst, and introduce 3-methylpyridine, chlorine gas and hydrogen fluoride to a chlorofluorination reaction zone to obtain a gas mixture containing 3-trifluoromethylpyridine;
   (2) Chlorination reaction: a temperature of chlorination is maintained at 220-380° C. in the presence of a chlorination catalyst, and introduce the gas mixture containing 3-trifluoromethylpyridine obtained in the step (1) into a chlorination reaction zone to obtain 2-chloro-5-trifluoromethylpyridine, the chlorination catalyst is a fluoride, an oxide, a hydroxide, a carbonate, a chloride of magnesium, calcium, barium, a supported palladium catalyst supported on activated carbon, alumina, or aluminum fluoride.

2. The method for preparing 2-chloro-5-trifluoromethylpyridine according to claim 1, wherein the chlorination catalyst is a fluoride, an oxide, a chloride of magnesium, calcium, a supported palladium catalyst supported on activated carbon, or aluminum fluoride.

3. The method for preparing 2-chloro-5-trifluoromethylpyridine according to claim 1, wherein the temperature of chlorofluorination is 220-260° C., and the temperature of chlorination is 270-320° C.

4. The method for preparing 2-chloro-5-trifluoromethylpyridine according to claim 1, wherein the molar ratio of 3-methylpyridine to chloride gas and to hydrogen fluoride is 1:0.1-50:1-30.

5. The method for preparing 2-chloro-5-trifluoromethylpyridine according to claim 1, wherein 3-methylpyridine is diluted with inert gas, and the molar ratio of 3-methylpyridine to inert gas is 1:0.5-50.

6. The method for preparing 2-chloro-5-trifluoromethylpyridine according to claim 1, wherein:
   the contact time of 3-methylpyridine, chloride gas and hydrogen fluoride with the chlorofluorination catalyst is 0.5-40 s in the step (1);
   the contact time of the gas mixture containing 3-trifluoromethylpyridine with the chlorination catalyst is 0.5-40 s in the step (2).

7. A method for preparing 2-chloro-5-trifluoromethylpyridine, wherein the method comprising:
   the first reaction temperature is maintained at 150-350° C. in the presence of a first catalyst, such that 3-trifluoromethylpyridine reacts with chlorine gas in gas phase to obtain 2-chloro-5-trifluoromethylpyridine;
   the first catalyst is at least one of ZSM-5, 5A, β or 13× molecular sieves,
   the Si/Al of the ZSM-5 molecular sieve is 50-300, and the balance cation is chosen from at least one of $H^+$, $Na^+$, $K^+$, $Ca^{2+}$.

8. The method for preparing 2-chloro-5-trifluoromethylpyridine according to claim 7, wherein the Si/Al of the ZSM-5 molecular sieve is 80-200, and the balance cation is at least one of $H^+$, $Na^+$ or $K^+$.

9. The method for preparing 2-chloro-5-trifluoromethylpyridine according to claim 7, wherein the first reaction temperature is 200-300° C.

10. The method for preparing 2-chloro-5-trifluoromethylpyridine according to claim 7, wherein the molar ratio of 3-trifluoromethylpyridine to chlorine gas is 1:0.1-20.

11. The method for preparing 2-chloro-5-trifluoromethylpyridine according to claim 7, wherein the contact time of 3-trifluoromethylpyridine and chlorine gas with the catalyst bed is 0.5-100 s.

12. A method for preparing 2-chloro-5-trifluoromethylpyridine, wherein the method comprising:
   the reaction temperature is maintained at 220-360° C. in the presence of a catalyst, such that 3-trifluoromethylpyridine and chlorine gas phase pass through a catalyst bed to obtain 2-chloro-5-trifluoromethylpyridine;
   the catalyst is a fluoride, an oxide, a hydroxide, a carbonate, a chloride of magnesium, calcium, barium, a supported palladium catalyst supported on activated carbon, alumina, or aluminum fluoride.

13. The method for preparing 2-chloro-5-trifluoromethylpyridine according to claim 1, wherein the reaction is carried out in a fixed bed or fluidized bed reactor.

14. The method for preparing 2-chloro-5-trifluoromethylpyridine according to claim 5, wherein the reaction is carried out in a fixed bed or fluidized bed reactor.

15. The method for preparing 2-chloro-5-trifluoromethylpyridine according to claim 12, wherein the reaction is carried out in a fixed bed or fluidized bed reactor.

* * * * *